United States Patent
Charrier et al.

(10) Patent No.: US 6,800,619 B2
(45) Date of Patent: Oct. 5, 2004

(54) CASPASE INHIBITORS AND USES THEREOF

(75) Inventors: Jean-Damien Charrier, Wantage (GB); Ronald Knegtel, Abingdon (GB); Michael Mortimore, Burford (GB)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 23 days.

(21) Appl. No.: 09/951,006

(22) Filed: Sep. 12, 2001

(65) Prior Publication Data
US 2002/0058630 A1 May 16, 2002

Related U.S. Application Data
(60) Provisional application No. 60/232,573, filed on Sep. 13, 2000.

(51) Int. Cl.[7] ......................... A61K 31/33; A61K 31/44; C07D 215/00; C07D 211/00; C07D 213/72
(52) U.S. Cl. ..................... 514/183; 514/315; 514/330; 514/331; 514/337; 514/356; 514/338; 514/339; 546/182; 546/245; 546/246; 546/247; 546/248; 546/262
(58) Field of Search ................................ 514/183, 315, 514/330, 331, 337, 356, 338, 339; 546/182, 245, 246, 247, 248, 262

(56) References Cited

U.S. PATENT DOCUMENTS 5,843,904 A * 12/1998 Bemis et al. .................. 514/18

FOREIGN PATENT DOCUMENTS

| EP | 644198 | * | 3/1995 |
|----|--------|---|--------|
| WO | WO 98/16502 | | 4/1998 |
| WO | WO 99/18781 | | 4/1999 |
| WO | WO 99/47154 | | 9/1999 |

OTHER PUBLICATIONS

Lipinsli et al, Biososteres in Drug Design, Annula Rep. in Med. Chem. 21,286–88(1986).*
Thornber,Isosterism and Molecular Modification in Drug Design, Chemical Soc. Review, 563–580 (1979).*
Coyle et al(Science vol. 219, 1184–1190(1983), "AD:A disorder of Cortical Cholinergic Innervation".*
Kin et al(PubMed Abstract 11112361, also cited as Clin. Immunol. 97/3,221–33(2000).*
Flores et al (PubMed 12014679, also cited as Anticancer 22/2A, 959–97(2002).*

* cited by examiner

*Primary Examiner*—Richard L. Raymond
*Assistant Examiner*—Sudhaker B. Patel
(74) *Attorney, Agent, or Firm*—Michael C. Badia; Vertex Pharmaceuticals Incorporated

(57) ABSTRACT

Described herein are compounds that are useful as caspase inhibitors having the formula:

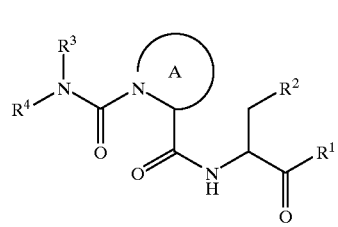

wherein Ring A is an optionally substituted piperidine, tetrahydroquinoline or tetrahydroisoquinoline ring; $R^1$ is hydrogen, CN, $CHN_2$, R, or $CH_2Y$; R is an optionally substituted group selected from an aliphatic group, an aryl group, or an aralkyl group; Y is an electronegative leaving group; $R^2$ is $CO_2H$, $CH_2CO_2H$, or esters, amides or isosteres thereof; and $R^3$ is hydrogen, an optionally substituted aryl group, an optionally substituted aralkyl group, or an optionally substituted $C_{1-6}$ aliphatic group, $R^4$ is an optionally substituted group selected from an aryl group or a heterocyclyl group, or $R^3$ and $R^4$ taken together with the nitrogen to which they are attached optionally form a substituted or unsubstituted monocyclic, bicyclic or tricyclic ring.

24 Claims, No Drawings

CASPASE INHIBITORS AND USES THEREOF

CROSS-REFERENCE TO RELATED APPLICATIONS

This application claims priority to U.S. Provisional Patent Application No. 60/232,573, filed Sep. 13, 2000.

FIELD OF THE INVENTION

This invention is in the field of medicinal chemistry and relates to novel compounds, and pharmaceutical compositions thereof, that inhibit caspases that mediate cell apoptosis and inflammation. The invention also relates to methods of using the compounds and pharmaceutical compositions of this invention to treat diseases where caspase activity is implicated.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders (see generally *Science*, 1998, 281, 1283–1312; Ellis et al., *Ann. Rev. Cell. Biol.*, 1991, 7, 663).

Caspases are a family of cysteine protease enzymes that are key mediators in the signaling pathways for apoptosis and cell disassembly (Thornberry, *Chem. Biol.*, 1998, 5, R97–R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

Caspase-1, the first identified caspase, is also known as interleukin converting enzyme or "ICE." Caspase-1 converts precursor interleukin-1β ("pIL-1β") to the pro-inflammatory active form by specific cleavage of pIL-1β between Asp-116 and Ala-117. Besides caspase-1 there are also eleven other known human caspases, all of which cleave specifically at aspartyl residues. They are also observed to have stringent requirements for at least four amino acid residues on the N-terminal side of the cleavage site.

The caspases have been classified into three groups depending on the amino acid sequence that is preferred or primarily recognized. The group of caspases, which includes caspases 1, 4, and 5, has been shown to prefer hydrophobic aromatic amino acids at position 4 on the N-terminal side of the cleavage site. Another group which includes caspases 2, 3 and 7, recognize aspartyl residues at both positions 1 and 4 on the N-terminal side of the cleavage site, and preferably a sequence of Asp-Glu-X-Asp. A third group, which includes caspases 6, 8, 9 and 10, tolerate many amino acids in the primary recognition sequence, but seem to prefer residues with branched, aliphatic side chains such as valine and leucine at position 4.

The caspases have also been grouped according to their perceived function. The first subfamily consists of caspases-1 (ICE), 4, and 5. These caspases have been shown to be involved in pro-inflammatory cytokine processing and therefore play an important role in inflammation. Caspase-1, the most studied enzyme of this class, activates the IL-1β precursor by proteolytic cleavage. This enzyme therefore plays a key role in the inflammatory response. Caspase-1 is also involved in the processing of interferon gamma inducing factor (IGIF or IL-18) which stimulates the production of interferon gamma, a key immunoregulator that modulates antigen presentation, T-cell activation and cell adhesion.

The remaining caspases make up the second and third subfamilies. These enzymes are of central importance in the intracellular signaling pathways leading to apoptosis. One subfamily consists of the enzymes involved in initiating events in the apoptotic pathway, including transduction of signals from the plasma membrane. Members of this subfamily include caspases-2, 8, 9 and 10. The other subfamily, consisting of the effector capsases 3, 6 and 7, are involved in the final downstream cleavage events that result in the systematic breakdown and death of the cell by apoptosis. Caspases involved in the upstream signal transduction activate the downstream caspases, which then disable DNA repair mechanisms, fragment DNA, dismantle the cell cytoskeleton and finally fragment the cell.

Knowledge of the four amino acid sequence primarily recognized by the caspases has been used to design caspase inhibitors. Reversible tetrapeptide inhibitors have been prepared having the structure $CH_3CO$-[P4]-[P3]-[P2]-CH(R)$CH_2CO_2H$ where P2 to P4 represent an optimal amino acid recognition sequence and R is an aldehyde, nitrile or ketone capable of binding to the caspase cysteine sulfhydryl. Rano and Thornberry, *Chem. Biol.* 4, 149–155 (1997); Mjalli, et al., *Bioorg. Med. Chem. Lett.* 3, 2689–2692 (1993); Nicholson et al., *Nature* 376, 37–43 (1995). Irreversible inhibitors based on the analogous tetrapeptide recognition sequence have been prepared where R is an acyloxymethylketone —$COCH_2OCOR'$. R' is exemplified by an optionally substituted phenyl such as 2,6-dichlorobenzoyloxy and where R is $COCH_2X$ where X is a leaving group such as F or Cl. Thornberry et al., *Biochemistry* 33, 3934 (1994); Dolle et al., *J Med. Chem.* 37, 563–564 (1994).

The utility of caspase inhibitors to treat a variety of mammalian diseases associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock. Yaoita et al., *Circulation*, 97, 276 (1998); Endres et al., *J Cerebral Blood Flow and Metabolism*, 18, 238, (1998); Cheng et al., *J. Clin. Invest.*, 101, 1992 (1998); Yakovlev et al., *J Neuroscience*, 17, 7415 (1997); Rodriquez et al., *J. Exp. Med.*, 184, 2067 (1996); Grobmyer et al., *Mol. Med.*, 5, 585 (1999).

In general, the peptidic inhibitors described above are very potent against some of the caspase enzymes. However, this potency has not always been reflected in cellular models of apoptosis. In addition peptide inhibitors are typically characterized by undesirable pharmacological properties such as poor oral absorption, poor stability and rapid metabolism. Plattner and Norbeck, in *Drug Discovery Technologies*, Clark and Moos, Eds. (Ellis Horwood, Chichester, England, 1990).

Recognizing the need to improve the pharmacological properties of the peptidic caspase inhibitors, peptidomimetic and non-natural amino acid peptide inhibitors have been reported.

WO 96/40647 discloses ICE inhibitors of the formula:

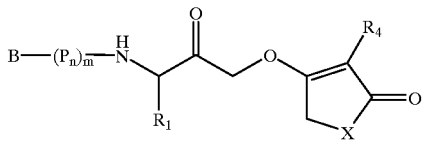

wherein B is H or an N-terminal blocking group; $R_1$ is the amino acid side chain of the $P_1$ amino acid residue wherein the $P_1$ amino acid is not Asp; $P_n$ is an amino acid residue or a heterocyclic replacement of the amino acid; $R_4$ is hydroxyl, alkoxyl, acyl, hydrogen, alkyl or phenyl; m is 0 or a positive integer; and X is N, S, O, or $CH_2$.

U.S. Pat. No. 5,585,357 discloses compounds which inhibit interleukin-1β protease. These inhibitors are represented by the formula:

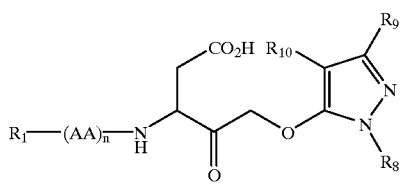

wherein each AA is independently L-valine or L-alanine; n is 0–2; $R_1$ is certain groups; and $R_8$, $R_9$, $R_{10}$ are each independently hydrogen, lower alkyl, halo substituted methyl, carbalkoxy, benzyl, phenyl or phenyl mono- or disubstituted with fluoro, nitro, methoxy, chloro, trifluoromethyl or methanesulfonyl.

WO 98/16502 discloses aspartate ester inhibitors of interleukin-1β converting enzyme of the formula:

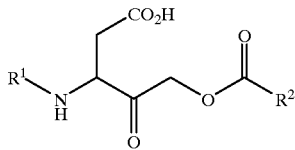

wherein $R^1$ is, inter alia, $R^5N(R^a)CHR^6CO-$; $R^2$ is certain groups; $R^6$ is H, $C_{1-6}$ alkyl, $-(CH_2)_n$, aryl, $-(CH_2)_nCO_2R^a$, hydroxyl substituted $C_{1-6}$ alkyl, or imidazole substituted $C_{1-6}$ alkyl; and $R^a$ is independently hydrogen, $C_{1-6}$ alkyl or $-(CH_2)_n$aryl WO 99/18781 discloses dipeptide apoptosis inhibitors having the formula:

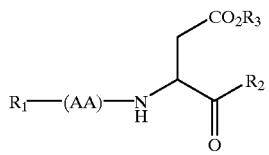

where $R_1$ is an N-terminal protecting group; AA is a residue of any natural α-amino acid, or β-amino acid; and $R_2$ and $R_3$ are defined in the application.

WO 00/023421 discloses (substituted)acyl dipeptide apoptosis inhibitors having the formula:

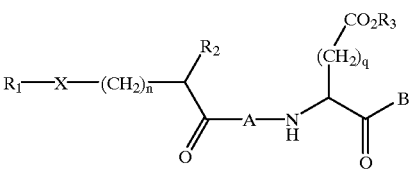

wherein n is 0, 1, or 2; q is 1 or 2; A is a residue of any natural or non-natural amino acid; B is a hydrogen atom, a deuterium atom, C1–10 straight chain or branched alkyl, cycloalkyl, phenyl, substituted phentyl, naphthyl, substituted naphthyl, 2-benzoxazolyl, substituted 2-oxazolyl, $(CH_2)_m$cycloalkyl, $(CH2)_m$phenyl, $(CH_2)_m$(substituted phenyl), $(CH2)_m$(1- or 2-naphthyl), $(CH_2)_m$heteroaryl, halomethyl, $CO_2R_{13}$, $CONR_{14}R_{15}$, $CH_2ZR_{16}$, $CH_2OCO$aryl, $CH_2OCO$(substituted aryl), $CH_2OCO$(heteroaryl), $CH_2OCO$(substituted heteroaryl), or $CH_2OPO(R_{17})R_{18}$, where $R_{13}$, $R_{14}$, $R_{15}$, $R_{16}$, $R_{17}$ and $R_{18}$ are defined in the application; $R_2$ is selected from a group containing hydrogen, alkyl, cycloalkyl, phenyl, substituted phenyl, $(CH_2)_mNH_2$; $R_3$ is hydrogen, alkyl, cycloalkyl, (cycloalkyl)alkyl, phenylalkyl, or substituted phenylalkyl; X is $CH_2$, C=O, O, S, NH, C=ONH or $CH_2OCONH$; and Z is an oxygen or a sulfur atom.

WO 00/061542 discloses dipeptide apoptosis inhibitors having the formula:

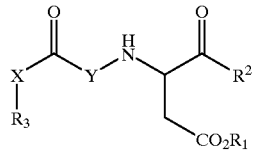

where $R_1$ is an optionally substituted alkyl or hydrogen group; $R_2$ is hydrogen or optionally substituted alkyl; Y is a residue of a natural or non-natural amino acid and $R_3$ is an alkyl, saturated carbocyclic, partially saturated carbocyclic, aryl, saturated heterocyclic, partially saturated heterocyclic or heteroaryl group, wherein said group is optionally substituted; X is O, S, $NR_4$, or $(CR_4R_5)_n$ where $R_4$ and $R_5$ are, at each occurrence, independently selected from the group consisting of hydrogen, alkyl and cycloalkyl, and n is 0, 1, 2, or 3; or X is $NR_4$, and $R_3$ and $R_4$ are taken together with the nitrogen atom to which they are attached to form a saturated heterocyclic, partially saturated heterocyclic or heteroaryl group, wherein said group is optionally substituted or X is $CR_4R_5$, and $R_3$ and $R_4$ are taken together with the carbon atom to which they are attached to form a saturated carbocyclic, partially saturated carbocyclic, aryl, saturated heterocyclic, partially saturated heterocyclic or oxygen-containing heteroaryl group, wherein said group is optionally substituted; and provided that when X is O, then $R_3$ is not unsubstituted benzyl or t-butyl; and when X is $CH_2$, then $R_3$ is not H.

While a number of caspase inhibitors have been reported, it is not clear whether they possess the appropriate pharmacological properties to be therapeutically useful. Therefore, there is a continued need for small molecule caspase inhibitors that are potent, stable, and penetrate membranes to provide effective inhibition of apoptosis in vivo. Such compounds would be extremely useful in treating the aforementioned diseases where caspase enzymes play a role.

SUMMARY OF THE INVENTION

It has now been found that compounds of this invention and pharmaceutical compositions thereof are particularly effective as inhibitors of caspases and cellular apoptosis. These compounds have the general formula I:

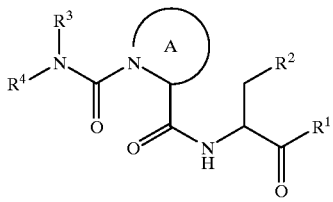

wherein:
Ring A is an optionally substituted piperidine, tetrahydroquinoline or tetrahydroisoquinoline ring;
$R^1$ is hydrogen, CN, $CHN_2$, R, or $CH_2Y$;
R is an optionally substituted group selected from an aliphatic group, an aryl group, or an aralkyl group;
Y is an electronegative leaving group;
$R^2$ is $CO_2H$, $CH_2CO_2H$, or esters, amides or isosteres thereof; and
$R^3$ is hydrogen, an optionally substituted aryl group, an optionally substituted aralkyl group, or an optionally substituted $C_{1-6}$ aliphatic group, $R^4$ is an optionally substituted group selected from an aryl group or a heterocyclyl group, or $R^3$ and $R^4$ taken together with the nitrogen to which they are attached optionally form is a substituted or unsubstituted monocyclic, bicyclic or, tricyclic ring.

The compounds of this invention have potent inhibition properties across a range of caspase targets with good efficacy in cellular models of apoptosis. In addition, these compounds are expected to have improved cell penetration and pharmacokinetic properties and, as a consequence of their potency, have improved efficacy against diseases where caspases are implicated.

DETAILED DESCRIPTION OF THE INVENTION

This invention provides novel compounds, and pharmaceutically acceptable derivatives thereof, that are particularly effective as caspase inhibitors. The invention also provides methods for using the compounds to treat caspase-mediated diseases in mammals. The compounds have the general formula I:

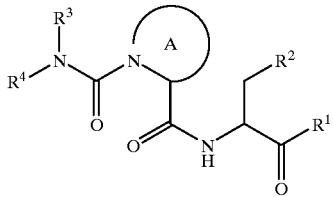

wherein:

Ring A is an optionally substituted piperidine, tetrahydroquinoline or tetrahydroisoquinoline ring;
$R^1$ is hydrogen, CN, $CHN_2$, R, or $CH_2Y$;
R is an optionally substituted group selected from an aliphatic group, an aryl group, or an aralkyl group;
Y is an electronegative leaving group;
$R^2$ is $CO_2H$, $CH_2CO_2H$, or esters, amides or isosteres thereof; and
$R^3$ is hydrogen, an optionally substituted aryl group, an optionally substituted aralkyl group, or an optionally substituted $C_{1-6}$ aliphatic group, $R^4$ is an optionally substituted group selected from an aryl group or a heterocyclyl group, or $R^3$ and $R^4$ taken together with the nitrogen to which they are attached optionally form a substituted or unsubstituted monocyclic, bicyclic or tricyclic ring.

As used herein, the following definitions shall apply unless otherwise indicated. The phrase "optionally substituted" may be used interchangeably with the phrase "substituted or unsubstituted" or with the term "(un)substituted." Unless otherwise indicated, an optionally substituted group may have one or more substituents that are independently selected.

The term "aliphatic" as used herein means straight chained, branched or cyclic $C_1$–$C_{12}$ hydrocarbons which are completely saturated or which contain one or more units of unsaturation. For example, suitable aliphatic groups include substituted or unsubstituted linear, branched or cyclic alkyl, alkenyl, or alkynyl groups and hybrids thereof such as (cycloalkyl)alkyl, (cycloalkenyl)alkyl or (cycloalkyl) alkenyl. The term "alkyl" used alone or as part of a group or larger moiety refers to both straight and branched chains containing one to twelve carbon atoms.

The term "halogen" means F, Cl, Br, or I. The term "heteroatom" means nitrogen, oxygen or sulfur.

The term "aryl" refers to monocyclic or polycyclic aromatic groups, and monocyclic or polycyclic heteroaromatic groups containing one or more heteroatoms, having five to fourteen atoms. Such groups include, but are not limited to, phenyl, naphthyl, anthryl, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, indolizinyl, indolyl, isoindolyl, indolinyl, benzofuranyl, benzothiophenyl, indazolyl, benzimidazolyl, benzthiazolyl, purinyl, quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, tetrahydrofuranyl, phthalimidinyl, tetrazolyl, and chromanyl.

The term "heterocyclic group" refers to saturated and partially unsaturated monocyclic or polycyclic ring systems containing one or more heteroatoms, wherein a monocyclic ring preferably has 5–7 ring atoms and a polycyclic ring preferably has 8–14 ring atoms. Such groups include, but are not limited to aziranyl, oxiranyl, azetidinyl, tetrahydrofuranyl, pyrrolinyl, pyrrolidinyl, dioxolanyl, imidazolinyl, imidazolidinyl, pyrazolinyl, pyrazolidinyl, pyranyl, piperidinyl, dioxanyl, morpholinyl, dithianyl, thiomorpholinyl, piperazinyl, trithianyl, quinuclidinyl, oxepanyl, and thiepanyl. The term "heterocyclic ring", whether saturated or unsaturated, also refers to rings that are optionally substituted.

An aryl group (including heteroaryl groups) or an aralkyl group, such as benzyl or phenethyl, may contain one or more substituents. Examples of suitable substituents on the unsaturated carbon atom of an aryl group include halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —$NO_2$, —CN, —N(R°)$_2$, —NR°C(O)R°, —NR°C(O)N (R°)$_2$, —NR°$CO_2$R°, —NR°NR°C(O)R°, —NR°NR°C(O) N(R°)$_2$, —NR°NR°$CO_2$R°, —C(O)C(O)R°, —C(O)$CH_2$C (O)R°, —$CO_2$R°, —C(O)R°, —C(O)N(R°)$_2$, —OC(O)N (R°)$_2$, —S(O)$_2$R°, —$SO_2$N(R°)$_2$, —S(O)R°, —NR°$SO_2$N (R°)$_2$, —NR°$SO_2$R°, —C(=S)N(R°)$_2$, —C(=NH) —N(R°)$_2$, —(CH$_2$)$_y$NHC(O)R°, —(CH$_2$)$_y$NHC(O)CH(V—

R°)(R°); wherein R° is H, a substituted or unsubstituted aliphatic group, preferably having 1–3 carbons, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon of an aliphatic group or of a non-aromatic heterocyclic ring include those listed above for the unsaturated carbon as well as the following: =O, =S, =NNHR$^+$, =NN(R$^+$)$_2$, =N—, =NNHC(O)R$^+$, =NNHCO$_2$(alkyl), =NNHSO$_2$(alkyl), or =NR$^+$, where each R$^+$ is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

A substitutable nitrogen on an aromatic or non-aromatic heterocyclic ring may be optionally substituted. Suitable substituents on the nitrogen include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is H, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Nitrogen and sulfur may be in their oxidized form, and nitrogen may be in a quaternized form.

The term "electronegative leaving group" has the definition known to those skilled in the art (see March, *Advanced Organic Chemistry*, 4$^{th}$ Edition, John Wiley & Sons, 1992). Examples of electronegative leaving groups include halogens such as F, Cl, Br, I, aryl- and alkylsulfonyloxy groups, trifluoromethanesulfonyloxy, —SR, —OPO(R$^5$)(R$^6$), where R is an aliphatic group, an aryl group, an aralkyl group, a carbocyclyl group, a carbocyclylalkyl group, a heterocyclyl group, or a heterocyclylalkyl group, and R$^5$ and R$^6$ are independently selected from R or OR.

When the R$^2$ group is in the form of an ester or amide, the present compounds undergo metabolic cleavage to the corresponding carboxylic acids, which are the active caspase inhibitors. Because they undergo metabolic cleavage, the precise nature of the ester or amide group is not critical to the working of this invention. The structure of the R$^2$ group may range from the relatively simple diethyl amide to a steroidal ester. Examples of the ester alcohol moiety of R$^2$ carboxylic acids include, but are not limited to, alcohols of C$_{1-12}$ aliphatic groups, such as C$_{1-6}$ alkyl or C$_{3-10}$ cycloalkyl, aryl groups, such as phenyl, aralkyl groups, such as benzyl or phenethyl, heterocyclyl or heterocyclylalkyl groups. Examples of suitable R$^2$ heterocyclyl groups include, but are not limited to, 5–6 membered heterocyclic rings having one or two heteroatoms such as piperidinyl, piperazinyl, or morpholinyl.

Amides of R$^2$ carboxylic acids may be primary, secondary or tertiary. Suitable substituents on the amide nitrogen include, but are not limited to, one or more groups independently selected from the aliphatic, aryl, aralkyl, heterocyclyl or heterocyclylalkyl groups described above for the R$^2$ ester alcohol. Likewise, other prodrugs are included within the scope of this invention. See Bradley D. Anderson, "Prodrugs for Improved CNS Delivery" in Advanced Drug Delivery Reviews (1996), 19, 171–202.

Isosteres or bioisosteres of carboxylic acids and esters or amides result from the exchange of an atom or group of atoms to create a new compound with similar biological properties to the parent carboxylic acid or ester. The bioisosteric replacement may be physicochemically or topologically based. An example of an isosteric replacement for a carboxylic acid is CONHSO$_2$(alkyl) such as CONHSO$_2$Me.

Compounds of this invention where R$^2$ is CO$_2$H or CH$_2$CO$_2$H, γ-ketoacids or δ-ketoacids respectively, may exist in solution as either the open form (a) or the cyclized hemiketal form (b) (y=1 for γ-ketoacids, y=2 for δ-ketoacids). The representation herein of either isomeric form is meant to include the other.

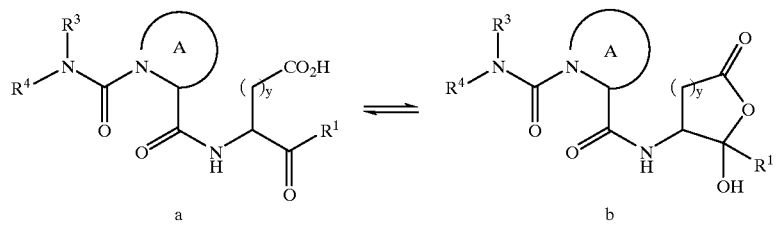

a        b

Likewise it will be apparent to one skilled in the art that certain compounds of this invention may exist in tautomeric forms or hydrated forms, all such forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

One embodiment of this invention relates to compounds of formula I wherein Ring A is an optionally substituted piperidine ring, represented by formula Ia:

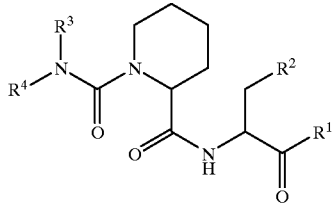

Ia

Another embodiment of this invention relates to compounds of formula I wherein Ring A is an optionally substituted tetrahydroquinoline ring, represented by formula Ib below:

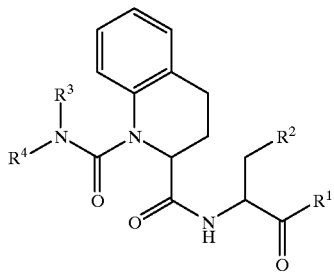

Ib

Another embodiment of this invention relates to compounds of formula I wherein Ring A is an optionally substituted tetrahydroisoquinoline ring are represented by formula Ic below:

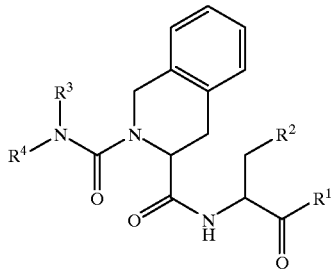

Ic

Ring A may be substituted or unsubstituted. Examples of suitable Ring A substituents include one or more groups selected from halogen, —R, —OR, —OH, —SR, protected OH (such as acyloxy), phenyl (Ph), substituted Ph, —OPh, substituted —OPh, —$NO_2$, —CN, —$NH_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is an aliphatic group or a substituted aliphatic group. Preferably R is a $C_{1-6}$ aliphatic group.

A preferred $R^1$ group is $CH_2Y$ where Y is an electronegative leaving group. Most preferably Y is F.

$R^3$ and $R^4$ may be taken together with the nitrogen to which they are attached to form a substituted or unsubstituted monocyclic, bicyclic or tricyclic ring. The $R^3R^4N$ ring system may be aromatic or non-aromatic and will have 1–6 heteroatoms selected from oxygen, nitrogen or sulfur. Preferably each ring of the $R^3R^4N$ ring system has 5–7 ring atoms Examples of such rings include indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

Preferred compounds of this invention have one or more, and more preferably all, of the features selected from the group consisting of:

(a) $R^1$ is $CH_2Y$ wherein Y is an electronegative leaving group;

(b) $R^2$ is $CO_2H$ or an ester or isosteres thereof; and (c) $R^3$ is hydrogen, an optionally substituted aryl group, an optionally substituted aralkyl group or an optionally substituted $C_{1-6}$ aliphatic group, $R^4$ is an optionally substituted group selected from an aryl group a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine. A preferred $R^3$ or $R^4$ aryl group is phenyl or a 5–6 membered heteroaromatic ring containing 1–3 heteroatoms selected from nitrogen, oxygen or sulfur. A preferred $R^3$ aralkyl group is a $C_{1-3}$ alkylidene chain substituted with a preferred aryl group. Preferred $R^4$ heterocyclyl groups include 5–6 membered rings containing 1–3 heteroatoms selected from nitrogen, oxygen or sulfur.

More preferred are compounds where Y is F and $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine. purine, quinolizine, quinoline, isoquinoline, cinnoline, phthalazine, quinazoline, quinoxaline, 1,8-naphthyridine, pteridine, quinuclidine, and phenazine. Even more preferred are compounds wherein $R^3R^4N$- ring system is carbazole, piperidine, indole, dihydroindole, phenothiazine, dihydrophenanthridine, phenoxazine, acridine, acridin-9-one, β-carboline, or 9-thia-2,10-diaza-anthracene. Most preferred are compounds wherein $R^3R^4N$— ring system is carbazole, phenothiazine, or dihydrophenanthridine.

The $R^3R^4N$— ring system may be optionally substituted. Examples of suitable substituents on the $R^3R^4N$— ring include one or more groups selected from halogen, —R, —OR, —OH, —SR, protected OH (such as acyloxy), phenyl (Ph), substituted Ph, —OPh, substituted —OPh, —$NO_2$, —CN, —$NH_2$, —NHR, —N(R)$_2$, —NHCOR, —NHCONHR, —NHCON(R)$_2$, —NRCOR, —NHCO$_2$R, —CO$_2$R, —CO$_2$H, —COR, —CONHR, —CON(R)$_2$, —S(O)$_2$R, —SONH$_2$, —S(O)R, —SO$_2$NHR, —NHS(O)$_2$R, =O, =S, =NNHR, =NNR$_2$, =N—OR, =NNHCOR, =NNHCO$_2$R, =NNHSO$_2$R, or =NR where R is an aliphatic group or a substituted aliphatic group. Preferably R is a $C_{1-6}$ aliphatic group.

Representative examples of compounds of the present invention are shown below in Table 1.

TABLE 1
Representative Compounds
Ia 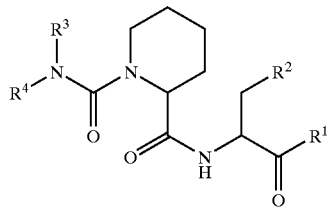
Ib 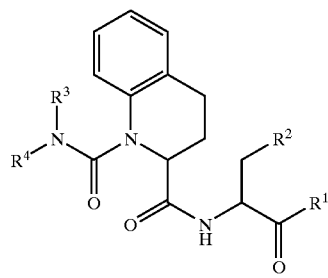
Ic 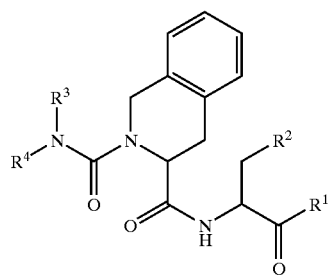
| No. | R¹ | R² | Ring A Type | R³R⁴N— |
|---|---|---|---|---|
| I-1 | $CH_2F$ | $CO_2H$ | Ia | phenothiazin-10-yl |
| I-2 | $CH_2F$ | $CO_2H$ | Ia | 2-chlorophenothiazin-10-yl |
| I-3 | $CH_2F$ | $CO_2H$ | Ia | 3-chlorophenothiazin-10-yl |
| I-4 | $CH_2F$ | $CO_2H$ | Ia | 3,4-dichlorophenothiazin-10-yl |

TABLE 1-continued

Representative Compounds

| I-5 | CH₂F | CO₂H | Ia | (2,7-dichloro-10-methyl-phenothiazine) |
| I-6 | CH₂F | CO₂H | Ia | (9-methyl-carbazole) |
| I-7 | CH₂F | CO₂H | Ia | (5-methyl-5,6-dihydrophenanthridine) |
| I-8 | CH₂F | CO₂H | Ia | (2,10-dimethyl-phenothiazine) |
| I-9 | CH₂F | CO₂H | Ia | (10-methyl-2-trifluoromethyl-phenothiazine) |
| I-10 | CH₂F | CO₂H | Ia | (2-methoxy-10-methyl-phenothiazine) |
| I-11 | CH₂F | CO₂NH₂ | Ia | (10-methyl-phenothiazine) |
| I-12 | CH₂F | CO₂NHEt | Ia | (10-methyl-phenothiazine) |
| I-13 | CH₂F | CO₂NEt₂ | Ia | (10-methyl-phenothiazine) |

TABLE 1-continued

Representative Compounds

| | | | |
|---|---|---|---|
| I-14 | $CH_2F$ | $CONHCH_2CH_2N(CH_3)_2$ | Ia |
| I-15 | $CH_2F$ | $CO_2H$ | Ib |
| I-16 | $CH_2F$ | $CO_2H$ | Ic |
| I-17 | $CH_2F$ | $CO_2H$ | Ib |
| I-18 | $CH_2F$ | $CO_2H$ | Ic |
| I-19 | $CH_2F$ | $CO_2H$ | Ia |
| I-20 | $CH_2F$ | $CO_2H$ | Ia |
| I-21 | $CH_2F$ | $CO_2H$ | Ia |
| I-22 | $CH_2F$ | $CO_2H$ | Ia |

TABLE 1-continued

Representative Compounds

| | | | | |
|---|---|---|---|---|
| I-23 | CH$_2$F | CO$_2$H | Ia | (2-chloro-10-methyl-10H-phenothiazine 5-oxide) |
| I-24 | CH$_2$F | CO$_2$H | Ia | (2-chloro-10-methyl-10H-phenothiazine 5,5-dioxide) |
| I-25 | CH$_2$F | CO$_2$H | Ia | (5-methyl-5H-pyrido[4,3-b]indole) |
| I-26 | CH$_2$F | CO$_2$H | Ia | (9-methyl-9H-pyrido[3,4-b]indole) |
| I-27 | CH$_2$F | CO$_2$H | Ia | (N-methyl pyrrolo-thiophene) |
| I-28 | CH$_2$F | CO$_2$H | Ia | (1-methyl-1H-indole) |
| I-29 | CH$_2$F | CO$_2$H | Ia | (6-chloro-1-methyl-1H-indole) |
| I-30 | CH$_2$F | CO$_2$H | Ia | (10-methyl-10H-pyrido-phenothiazine) |

The compounds of this invention may be prepared in general by methods known to those skilled in the art for analogous compounds, as illustrated by the general Scheme I below and by the preparative examples that follow.

Scheme I

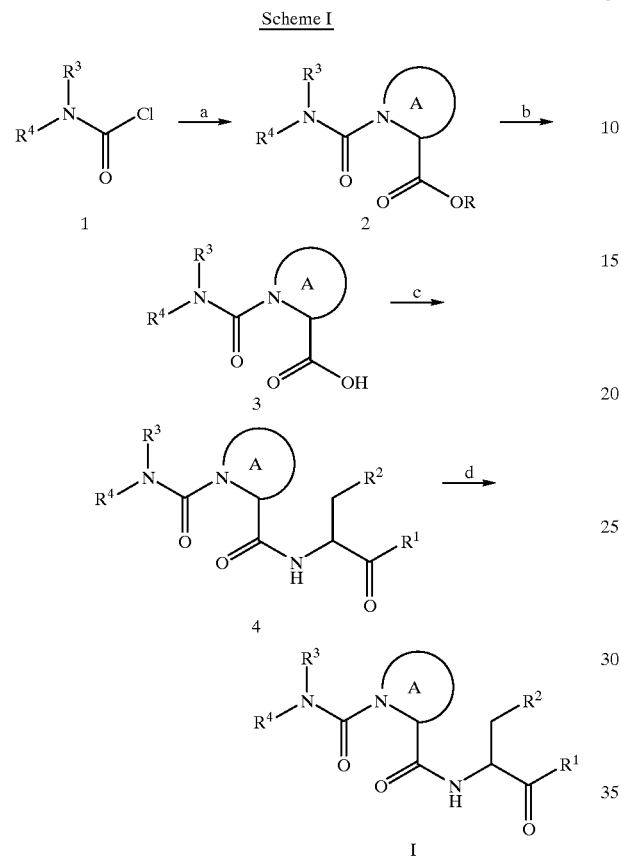

Reagents: (a) H—(Ring A)—CO$_2$R; (b) NaOH, THF, H$_2$O; (c) H$_2$NCH(CH$_2$R$^2$)CH(OH)R$^1$; EDC, N,N-dimethylaminopyridine, 1-hydroxybenzotriazole; (d) i. Dess-Martin periodinane; ii. trifluoroacetic acid, dichloromethane.

Scheme I above shows a general route for preparing compounds of this invention. The carbamoyl chloride 1 (or an analogous isocyanate) may be coupled with an amino acid ester, H—(Ring A)—CO$_2$R to provide urea 2. Hydrolysis of the ester 2 provides acid 3. If the ester is a tert-butyl ester then it may be hydrolyzed with acid such as trifluoroacetic acid. The acid 3 may then be coupled with an appropriate amino alcohol, H$_2$NCH(CH$_2$R$^2$)CH(OH)R$^1$ to provide 4. In step c, "EDC" is 1-(3-dimethylaminopropyl)-3-ethylcarbodiimide. Depending on the nature of R$^1$ an amino ketone may be used, in place of the amino alcohol, which avoids the subsequent oxidation step. In the case of fluoromethyl ketones where R$^2$ is CO$_2$tBu, the amino alcohol may be obtained according to the method of Revesz et al., *Tetrahedron Lett.*, 1994, 35, 9693. The hydroxyl in compound 4 is oxidized to compound I which may be further modified, depending on the nature of R$^2$, according to methods generally known in the art for analogous compounds. For example, if the product I requires R$^2$ to be a carboxylic acid, then R$^2$ in 4 is preferably an ester and the further step is a hydrolysis of the ester group.

Certain useful intermediates for making compounds of this invention may be obtained as follows. Substituted phenothiazines are either commercially available or may be prepared as described by J. I. G. Cadogan, S. Kulik, C. Thomson and M. J. Todd, *J. Chem. Soc.*, 1970, 2437–2441. 9,10-Dihydrophenanthridine was prepared according to G. M. Badger, J. H. Seidler and B. Thomson, *J. Chem. Soc*, 1951, 3207–3211. Carbamoyl chlorides are either commercially available or may be prepared as described by R. Dahlbom and B. Bjorkqvist, Acta Chem. Scand., 15, 1961, 2043–2046.

SYNTHETIC EXAMPLES

Example 1

[3S/R, (2S)]-5-Fluoro-4-oxo-3-{[1-(phenothiazine-10-carbonyl)piperidine-2-carbonyl]amino}-pentanoic acid

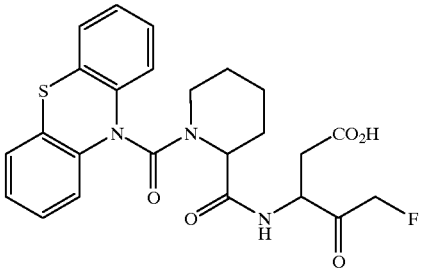

Method A (S)-(1-Phenothiazine-10-carbonyl)piperidine-2-carboxylic acid methyl ester

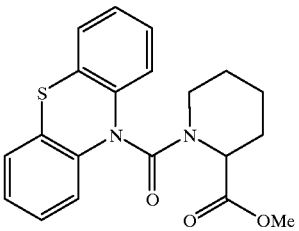

To a stirred solution of methyl pipecolate hydrochloride (1 g, 5.57 mmol) in THF (10 ml) was added phenothiazine carbonyl chloride (1.457 g, 5.57 mmol) followed by diisopropylethylamine (2.02 mL, 11.68 mmol). The resulting solution was stirred for 16 h before being partitioned between ethyl acetate and aq. sat. NH$_4$Cl. The organic layer was washed with brine, dried (MgSO$_4$), filtered and evaporated. The residue was purified by flash chromatography (15% ethyl acetate in hexane) to afford the sub-title compound as a colorless oil which crystallized upon standing (1.823 g, 89%): $^1$H NMR (400 MHz, CDCl$_3$) δ 1.13–1.48 (3H, m), 2.57–2.69 (2H, m), 2.16 (1H, m), 3.00 (1H, m), 3.74 (4H, s+m), 5.00 (1H, m), 7.11 (2H, t), 7.22–7.34 (4H, m), 7.76 (2H, d); $^{13}$C NMR (100 MHz, CDCl$_3$) δ 21.3 (CH$_2$), 24.8 (CH$_2$), 27.3 (CH$_2$), 44.9 (CH$_2$), 52.5 (CH$_3$), 55.9 (CH), 122.8 (CH), 125.5 (CH), 127.8 (CH), 128.0 (CH), 129.2 (C), 141.7 (C), 158.4 (C), 172.2 (C).

Method B

(S)-(1-Phenothiazine-10-carbonyl)piperidine-2-carboxylic acid

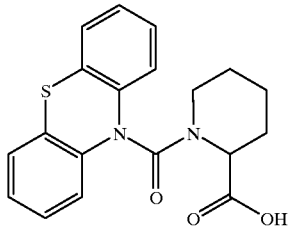

To a stirred solution of (S)-(1-phenothiazine-10-carbonyl)piperidine-2-carboxylic acid methyl ester (0.912 g) in THF (15 ml) and water (8 ml) was added 2M NaOH (3.71 mL) and the reaction mixture was stirred for 16 hours. The reaction mixture was poured into sodium hydrogen carbonate solution (50 ml) and extracted with ethyl acetate (40 ml). Aqueous phase made acidic and extracted with ethyl acetate (2×75 ml). Organic extracts combined, dried (MgSO$_4$) and concentrated to eave the subtitle compound as a white solid (0.709 g, 81%): $^1$H NMR (400 MHz, CDCl$_3$) δ 0.99–1.72 (5H, m), 2.23 (1H, m), 2.97 (1H, m), 3.58 (1H, m), 4.93 (1H, m), 7.16 (2H, t), 7.28 (2H, t), 7.37 (2H, d), 7.78 (2H, d); $^{13}$C NMR (100 MHz, CDCl$_3$) δ 21.0 (CH$_2$), 24.2 (CH$_2$), 26.7 (CH$_2$), 45.7 (CH$_2$), 56.0 (CH), 123.8 (CH), 126.0 (CH), 127.9 (CH), 128.1 (CH), 130.3 (C), 141.2 (C), 160.1 (C), 175.9 (C).

Method C

[3S/R, 4S/R (2S)]-5-Fluoro-4-hydroxy-3-{[1-(phenothiazine-10-carbonyl)piperidine-2-carbonyl]amino}-pentanoic acid tertbutyl ester

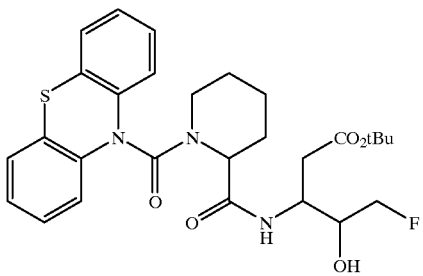

A stirred mixture of (S)-(1-phenothiazine-10-carbonyl)piperidine-2-carboxylic acid (233 mg, 0.658 mmol), 3-amino-5-fluoro-4-hydroxy-pentanoic acid tert-butyl ester (150 mg, 0.724 mmol), HOBt (98 mg, 0.724 mmol), DMAP (88 mg, 0.724 mmol) and anhydrous THF (10 mL) was cooled to 0° C. then EDC (139 mg, 0.724 mmol) was added. The mixture was allowed to warm to room temperature during 16 h then concentrated under reduced pressure. The residue was purified by flash chromatography (50% ethyl acetate in hexane) to afford the sub-title compound as a pale pink foam (294 mg, 82%): $^1$H NMR (400 MHz, CDCl$_3$) δ 1.96 (1H, m), 1.18–1.60 (13H, m), 2.10–2.25 (1H, m), 2.48–2.70 (2H, m), 2.78–2.94 (1H, m), 3.51–4.72 (7H, m), 7.03–7.36 (7H, m), 7.71–7.76 (2H, m); $^{19}$F (376 MHz, CDCl$_3$) δ −228.9 (t), −229.3 (t), −230.1 (t), −230.2 (t).

Method D

[3S/R, (2S)]-5-Fluoro-4-oxo-3-{[1-(phenothiazine-10-carbonyl)piperidine-2-carbonyl]amino}-pentanoic acid tert-butyl ester

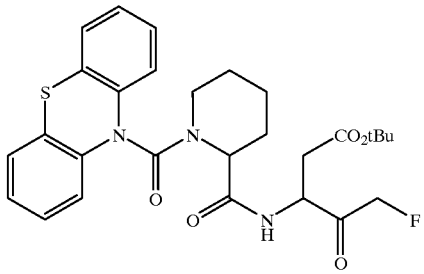

A stirred solution of [3S/R, 4S/R (2S)]-5-fluoro-4-hydroxy-3-{[1-(phenothiazine-10-carbonyl)piperidine-2-carbonyl]amino}-pentanoic acid tertbutyl ester (294 mg, 0.541 mmol) in anhydrous DCM (10 mL) was treated with 1,1,1-triacetoxy-1,1-dihydro-1,2-benziodoxol-3(1H)-one (344 mg, 0.812 mmol) at 0° C. The resulting mixture was allowed to warm to room temperature over 2 h, diluted with ethyl acetate, then poured into a 1:1 mixture of saturated aqueous sodium hydrogen carbonate and saturated aqueous sodium thiosulphate. The organic layer was removed and the aqueous layer re-extracted with ethyl acetate. The combined organic extracts were dried (Na$_2$SO$_4$) and concentrated. The residue was purified by flash chromatography (30% ethyl acetate in hexane) to afford the sub-title compound as a pale pink foam (220 mg, 75%): $^1$H NMR (400 MHz, CDCl$_3$) δ 0.84–0.96 (1H, m), 1.20–1.40 (10H, m+2s), 1.51–1.56 (3H, m), 2.20–2.27 (1H, m), 2.70–2.98 (3H, m), 3.49–3.63 (1H, m), 4.74–5.24 (4H, m), 7.14–7.18 (2H, m), 7.28–7.38 (4H, m), 7.48–7.79 (3H, m); $^{13}$C (100 MHz, CDCl$_3$) δ 20.8/21.0 (CH$_2$), 23.7/23.9 (CH$_2$), 25.8/25.9 (CH$_2$), 28.2/28.3 (CH$_3$), 36.8/36.9 (CH$_2$), 46.0/46.1 (CH$_2$), 52.9 (CH), 56.8 (CH), 82.6 (C), 84.4/84.5 (2d, J 184.0/183.3, CH$_2$F), 123.7/123.8 (CH), 126.1 (CH), 128.0/128.1 (CH), 128.2/128.3 (CH), 130.4/130.5 (C), 141.4 (C), 160.0 (C), 170.0 (C), 171.7 (C), 202.9 (C); $^{19}$F (376 MHz, CDCl$_3$) δ −231.9 (t), −232.2 (t).

Method E

[3S/R, (2S)]-5-Fluoro-4-oxo-3-{[1-(phenothiazine-10-carbonyl)piperidine-2-carbonyl]amino}-pentanoic acid

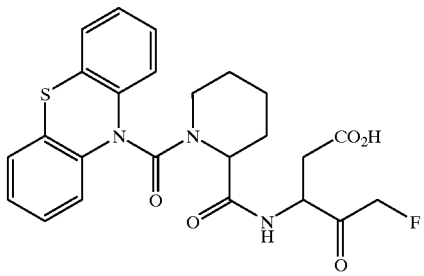

Trifluoroacetic acid (5 mL) was added to a stirred ice cold solution of [3S/R, (2S)]-5-fluoro-4-oxo-3-{[1-(phenothiazine-10-carbonyl)piperidine-2-carbonyl]amino}-pentanoic acid tert-butyl ester (130 mg, 0.24 mmol) in anhydrous DCM (5 mL). The mixture was stirred at 0° C. for 0.5 h then at room temperature for 0.5 h. The mixture was concentrated under reduced pressure and then the residue was dissolved in dry DCM. This process was repeated several times in order to remove excess trifluoroacetic acid. The gum was lyophilized twice from HPLC grade water to afford the title compound as a white powder (77 mg, 66%): IR (solid) 1670, 1716, 1782 cm$^{-1}$; $^1$H NMR (400 MHz, d$_6$-DMSO) δ 0.96–0.99 (1H, m), 1.23–1.26 (2H, m), 1.42–1.44 (1H, m), 1.60 (1H, m), 1.91–1.98 (1H, m), 2.51–2.89 (2H, m), 3.11–3.22 (1H, m), 3.57–3.60 (1H, m), 4.30–4.72 and 5.05–5.29 (4H, 2 m), 7.11–7.17 (2H, m), 7.24–7.30 (2H, m), 7.34–7.38 (2H, m), 7.57–7.63 (2H, m), 8.07–8.61 (1H, m); $^{13}$C NMR (100 MHz, DMSO) δ (DMSO+TFA) 18.8/18.9 (CH$_2$), 22.2/22.3 (CH$_2$), 25.8/26.1 (CH$_2$), 31.5/33.2 (CH$_2$), 43.2 (CH$_2$), 50.6/51.1 (CH), 54.4/54.5 (CH), 82.8/82.9 (2d, J 178.6/178.1, CH$_2$F), 119.9/120.0 (CH), 120.4/120.5 (CH), 124.0/124.1 m(CH), 125.9/126.0 (C), 126.4/126.5 (CH), 139.6/139.7 (C), 156.0/156.4 (CO), 170.3 (CO), 170.7/170.8 (CO), 202.2/202.3 (2d, J 14.6/15.1, CO).; $^{19}$F (376 MHz, DMSO) δ chemical shift (multiplicity, relative intensity) −226.7 (t, 3), −226.9 (t, 3), −230.4 (t, 1), −231.2 (t, 1), −232.7 (t, 10), −233.0 (t, 10).

Example 2

[3S/R, (2S)]-3-{[1-(2-Chlorophenothiazine-10-carbonyl)piperidine-2-carbonyl]amino}-4-fluoro-4-oxo-pentanoic acid

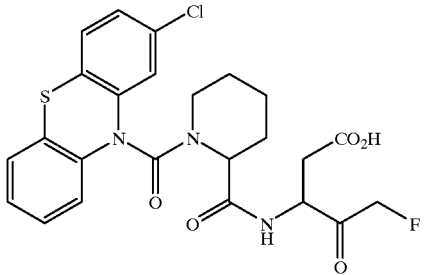

This was prepared from 2-chlorophenothiazine carbonyl chloride using procedures similar to those described above in Methods A–E (73 mg, 69%): IR (solid, cm-1) 1738, 1660, 1555, 1363, 1224 ; $^1$H NMR (400 MHz, d$_6$-DMSO+TFA) δ 0.98–1.61 (4H, m), 1.94–2.03 (1H, m), 2.53–2.89 (2H, m), 3.12–3.24 (1H, m), 3.51–3.61 (1H, m), 4.31–4.73 and 5.10–5.24 (4H, 2m), 7.15–7.49 (6H, m), 7.77–7.81 (1H, m), 8.13–8.64 (1H, m) ; $^{13}$C NMR (100 MHz, DMSO+TFA) δ 18.7/18.8 (CH$_2$), 22.3/22.6 (CH$_2$), 25.9/26.2 (CH$_2$), 31.5/33.2 (CH$_2$), 43.0/43.2 (CH$_2$), 50.6/51.1 (CH), 54.4/54.5 (CH), 82.8/82.9 (2d, J 178.7/178.3, CH$_2$F), 119.3/119.8 (CH), 120.2/120.3 (CH), 123.6/123.7 (CH), 124.4/124.5 (CH), 124.6/124.8 (C), 126.6 (CH), 126.9 (CH), 127.5 (CH), 131.0 (C), 139.2/139.2 (C), 140.7/140.7 (C), 155.5/155.9 (C), 170.1/170.2 (C), 170.7/170.8 (C), 201.2/201.3 (2d, J 14.3/13.9, CO) ; $^{19}$F NMR (376 MHz, DMSO+TFA) δ −226.7 (t), −226.9 (t), −230.3 (t), −232.7 (t), −233.0 (t)

Example 3

[3S/R, (2S)]-3-{[1-(3-Chlorophenothiazine-10-carbonyl)piperidine-2-carbonyl]amino}-4-fluoro-4-oxo-pentanoic acid

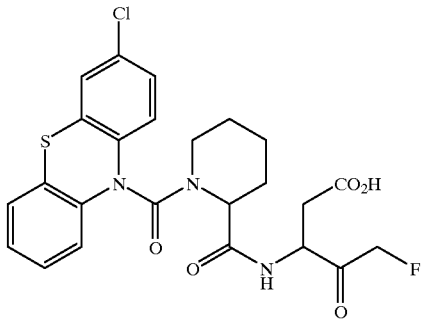

This was prepared from 3-chlorophenothiazine carbonyl chloride using procedures similar to those described above in Methods A–E (108 mg, 65%): IR (solid, cm-1) 1737, 1655, 1455, 1373, 1224 ; $^1$H NMR (400 MHz, d$_6$-DMSO+TFA) δ 0.99–1.61 (5H, m), 1.91–2.04 (1H, m), 2.54–2.90 (2H, m), 3.12–3.24(1H, m), 3.48–3.60 (1H, m), 4.26–5.28 (4H, m), 7.15–7.68 (7H, m), 8.10–8.62 (1H, m) ; $^{13}$C NMR (100 MHz, DMSO+TFA) δ 18.8 (CH$_2$), 22.2/22.3 (CH$_2$), 25.8 (CH$_2$), 33.1/33.2 (CH$_2$), 43.2 (CH$_2$), 50.6/51.0 (CH), 54.3/54.4 (CH), 82.7/82.8 (2d, CH$_2$F), 120.2/120.3 (CH), 121.3/121.4 (CH), 124.2/124.3 (CH), 124.8/125.0 (C), 125.7 (CH), 126.3 (CH), 126.6 (CH), 126.8 (CH), 127.7/127.9 (C), 127.9/128.0 (C), 138.5 (C), 139.3 (C), 156.0 (CO), 170.1 (CO), 170.6/170.7 (CO), 201.1/201.2 (2d, CO).; $^{19}$F NMR (376 MHz, DMSO+TFA) δ −226.6 (t), −226.9 (t), −232.6 (t), −232.9 (t), Example 4

[3S/R, (2S)]-3-{[1-(3,4-Dichlorophenothiazine-10-carbonyl)piperidine-2-carbonyl]amino}-4-fluoro-4-oxo-pentanoic acid

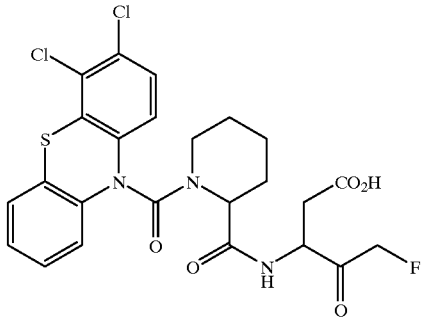

The title compound was prepared from 3,4-dichlorophenothiazine carbonyl chloride using procedures similar to those described above in Methods A–E (91 mg, 66%): IR (solid, cm-1) 1737, 1439, 1363, 1219 ; $^1$H NMR (400 MHz, d$_6$-DMSO+TFA) δ 1.03–1.62 (5H, m), 1.97–2.06 (1H, m), 2.54–2.86 (2H, m), 3.14–3.28 (1H, m), 3.59–3.66 (1H, m), 4.30–5.26 (4H, m), 7.15–7.68 (6H, m), 8.14–8.96 (1H, m) ; $^{13}$C NMR (100 MHz, DMSO+TFA) δ 20.2 (CH$_2$), 23.8 (CH$_2$), 27.3 (CH$_2$), 34.6/34.7 (CH$_2$), 44.5 (CH$_2$), 52.1/52.5 (CH), 55.7/55.9 (CH), 84.2/84.3 (2d, CH$_2$F), 120.2/

120.3 (CH), 120.8/120.9 (CH), 124.2/124.4 (C), 125.9 (CH), 127.7/127.8 (C), 128.2 (CH), 128.4/128.5 (C), 128.8 (CH), 128.9 (CH), 140.0 (C), 140.1 (C), 140.6 (C), 156.8/156.8 (CO), 171.5 (CO), 172.1/172.1 (CO), 202.6/202.7 (2d, CO); $^{19}$F NMR(376 MHz, DMSO+TFA) δ −226.6 (t), −226.8 (t), −232.6 (t), −232.9 (t).

Example 5

[3S/R, (2S)]-3-{[1-(2,6-Dichlorophenothiazine-10-carbonyl)piperidine-2-carbonyl]amino}-4-fluoro-4-oxo-pentanoic acid

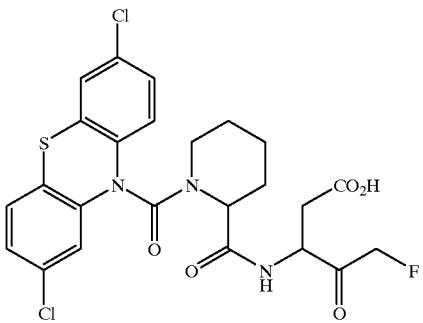

The title compound was prepared from 2.7-dichlorophenothiazine carbonyl chloride using procedures similar to those described above in Methods A-E (91 mg, 70%): IR (solid, cm−1) 1737, 1660, 1555, 1363, 1224; $^{1}$H NMR (400 MHz, d$_{6}$-DMSO+TFA) δ 1.02–1.62 (5H, m), 1.91–2.02 (1H, m), 2.53–2.90 (2H, m), 3.13–3.25 (1H, m), 3.51–3.62 (1H, m), 4.31–5.29 (4H, m), 7.22–7.75 (6H, m), 8.18–8.65 (1H, m) ; $^{13}$C NMR (100 MHz, DMSO+TFA) δ 20.2 (CH$_{2}$), 23.8 (CH$_{2}$), 27.3 (CH$_{2}$), 34.6 (CH$_{2}$), 44.7 (CH$_{2}$), 52.5 (CH), 55.8 (CH), 84.3 (d, J 178.2, CH$_{2}$F), 120.7/121.2 (CH), 122.7/122.8 (CH), 124.7/125.1 (C), 125.3/125.4 (CH), 127.4 (CH), 128.1 (CH), 128.7/128.9 (C), 129.1 (CH), 129.8 (C), 132.7 (C), 139.5/139.6 (C), 141.8/141.9 (C), 157.0 (CO), 171.5 (CO), 172.1 (CO), 202.6 (d, J 14.3, CO); $^{19}$F NMR(376 MHz, DMSO+TFA) δ −226.6 (t), −226.9 (t), −232.6 (t), −232.9 (t).

Example 6

[3S/R, (2S)]-3-{[1-(Carbazole-9-carbonyl)piperidine-2-carbonyl]amino}-4-fluoro-4-oxo-pentanoic acid

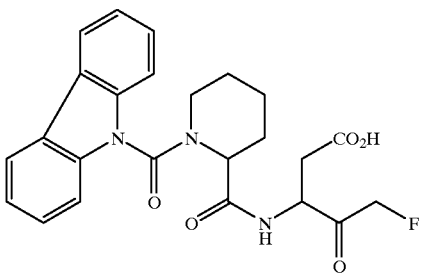

The title compound was prepared from 9-carbazole carbonyl chloride using procedures similar to those described above in Methods A-E (180 mg, 75%): IR (solid, cm−1) 1737, 1655, 1419, 1373, 1224 ; $^{1}$H NMR (400 MHz, d$_{6}$-DMSO+TFA) δ 1.36–1.65 (6H, m), 1.94–1.99 (1H, m), 2.12–2.21 (1H, m), 2.59–2.89 (2H, m), 4.32–5.27 (4H, m), 7.30–7.36 (2H, m), 7.48–7.54 (2H, m), 7.63–7.76 (2H, m), 8.17–8.72 (3H, m) ; $^{13}$C NMR (100 MHz, DMSO+TFA) δ 19.0 (CH$_{2}$), 23.7/23.8 (CH$_{2}$), 26.5/26.8 (CH$_{2}$), 33.3/33 .5 (CH$_{2}$), 44.1 (br, CH$_{2}$), 50.9/51.4 (CH), 54.5 (br, CH),82.9/83.1 (2d, J 178.7/178.7, CH$_{2}$F), 111.0/111.1 (CH), 111.9 (CH), 119.5/119.7 (CH), 120.6/120.7 (CH), 122.5/122.7 (C), 125.8/125.9 (CH), 137.1/137.4 (C), 153.2/153.3 (C), 170.3/170.4 (C), 170.8/170.9 (C), 201.4/201.5 (2d, J 14.6/14.6, CO) ; $^{19}$F NMR (376 MHz, DMSO+TFA) δ d (J, %I) −226.6 (t, 3), −226.8 (t, 3), −230.0 (t, 1), −232.7 (t, 10), −232.7 (t, 10).

Example 7

[3S/R, (2S)]-5-Fluoro-4-oxo-3-{[1-(6H-phenanthridine-5-carbonyl)-piperidine-2-carbonyl]amino}-pentanoic acid

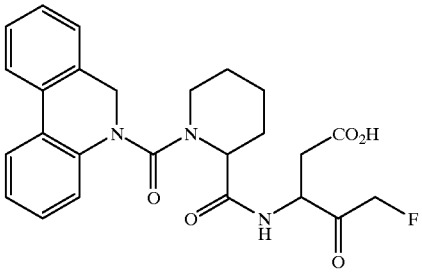

The title compound was prepared from 9,10-dihydrophenanthrinine carbonyl chloride using procedures similar to those described above in Methods A–E (115 mg, 61%): IR (solid, cm−1) 1731, 1419, 1363, 1219; $^{1}$H NMR (400 MHz, d$_{6}$-DMSO+TFA) δ 1.27–1.69 (5H, m), 1.90–2.06 (1H, m), 2.55–2.87 (2H, m), 3.13–3.21 (2H, m), 4.31–5.26 (6H, m), 7.12–7.48 (6H, m), 7.84–7.86 (2H, m), 8.08–8.58 (1H, m) ; $^{13}$C NMR (100 MHz, DMSO+TFA) δ 20.5 (CH$_{2}$), 24.2 (CH$_{2}$), 27.73 (CH$_{2}$), 34.6/34.8 (CH$_{2}$), 44.9 (CH$_{2}$), 48.5/48.7 (CH), 52.1/52.5 (CH), 55.4/55.7 (CH), 84.2 (d, CH$_{2}$F), 120.2 (CH), 123.3 (CH), 123.6 (CH), 124.7 (CH), 126.1 (C),126.3 (CH), 128.0 (CH), 128.3 (CH), 128.7 (CH), 131.6 (C), 134.6 (C), 140.2 (C), 172.1/172.2 (CO), 172.4/172.4 (CO), 203.0 (d, CO) ; $^{19}$F NMR(376 MHz, DMSO+TFA) δ −226.8 (t), −226.9 (t), −232.7 (t), −232.9 (t).

Example 8

[3S/R, (2S)]-3-{[1-(2-Methylphenothiazine-10-carbonyl)piperidine-2-carbonyl]amino}-4-fluoro-4-oxo-pentanoic acid

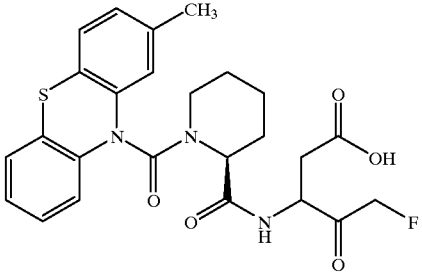

The title compound was prepared from 2-methylphenothiazine carbonyl chloride using procedures similar to those described above in Methods A–E (3.7 mg, 17%): ¹H NMR (400 MHz, d₆-DMSO) δ 0.86–1.75 (7H, m), 1.91–2.80 (5H, m), 3.13–3.66 (2H, m), 4.13–4.77 (2H, m), 5.06–5.33 (1H, m), 6.96–8.61(8H, m); ¹³C NMR (100 MHz, d₆-DMSO) δ 201.3, 201.2, 201.0, 171.8, 170.7, 170.6, 170.2, 169.8, 169.7, 156.2, 155.8, 139.7, 139.6, 139.6, 139.5, 136.1, 127.5, 125.9, 122.3, 122.2, 120.6, 119.8, 83.7, 83.6, 81.9, 81.8, 66.2, 53.8, 50.5, 43.1, 33.1, 28.6, 26.1, 25.9, 22.5, 22.3, 22.2, 22.1, 21.2 and 18.9; ¹⁹F NMR (376 MHz, d₆-DMSO) δ −226.7, −226.8, −230.2, −231.2, −232.7, −233.0.

Example 9

[3S/R, (2S)]-3-{[1-(2-Trifluoromethylphenothiazine-10-carbonyl) piperidine-2-carbonyl]amino}-4-fluoro-4-oxo-pentanoic acid

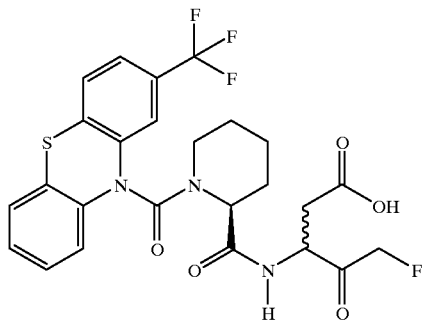

The title compound was prepared from 2-trifluoromethylphenothiazine carbonyl chloride using procedures similar to those described above in Methods A–E (1.78 g, 98%):IR (solid, cm⁻¹) 1792.9, 1654.6, 1465.2, 1403.7, 1321.8, 1224.5, 1163.0, 1116.9; ¹H NMR (400 MHz, d₆-DMSO) δ 0.76–1.09 (1H, m), 1.20–1.69 (4H, m), 1.87–2.10 (1H, m), 2.50–2.98 (2H, m), 3.18 (1H, m), 3.41–3.62 (1H, m), 4.26–4.80 (2.75H, m), 5.02–5.32 (1.25H, m), 7.17–7.64 (6H, m), 8.03–8.20 (1H, m), 8.43–8.68 (1H, brm), 12.50 (1H, brs); ¹⁹F NMR (376 MHz, d₆-DMSO) δ −61.6, −61.64, −61.7, −226.8, −226.9, −230.2, −231.3, −232.8, −233.1.

Example 10

[3S/R, (2S)]-3-{[1-(2-Methoxyphenothiazine-10-carbonyl)piperidine-2-carbonyl]amino}-4-fluoro-4-oxo-pentanoic acid

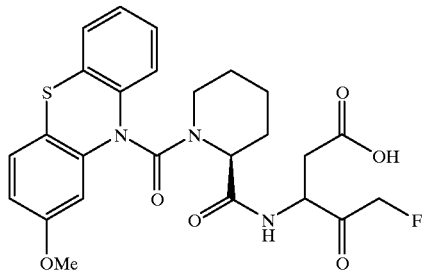

The title compound was prepared from 2-methoxyphenothiazine carbonyl chloride using procedures similar to those described above in Methods A–E (21 mg, 4%):IR (solid, cm⁻¹) 1174.6, 1205.4, 1263.8, 1405.7, 1442.81, 1463.7, 1596.9, 1652.8; ¹H NMR (400 MHz, CDCl₃) δ 1.1 (1H, m), 1.3 (1H, m), 1.5–1.7 (3H, m), 2.15 (1H, m), 2.7–3.0 (3H, m), 3.60 (1H, t), 3.85 (3H, s), 4.6–4.9 (4H, m), 6.75 (1H, d), 7.1–7.7 (7H, m) ; ¹³C NMR (100 MHz, CDCl₃) δ 20.9, 23.9, 26.0, 46.1, 56.1, 57.1, 109.8, 112.1, 112.2, 123.6, 126.9, 126.2, 127.9, 128.3, 128.6, 128.7, 141.1, 141.2, 142.4, 159.8, 159.9; ¹⁹F NMR (376 MHz, CDCl₃) δ −231.09 and −230.76.

Example 11

[3S/R, (2S)]-5-Fluoro-4-oxo-3-{[1-(phenothiazine-10-carbonyl)piperidine-2-carbonyl]amino}-pentamide

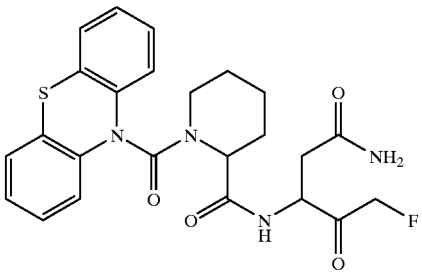

To a stirred mixture of [3S/R, (2S)]-5-Fluoro-4-oxo-3-{[1-(phenothiazine-10-carbonyl)piperidine-2-carbonyl]amino}-pentanoic acid (200 mg, 0.4 mmol), prepared as in Example 1, in anhydrous THF (4ml), was added EDC (84 mg, 0.44 mmol), and a solution of the ammonia in 1,4 dioxane (0.8 ml of a 0.5M solution, 4 mmol). The mixture was stirred at room temperature for 16 h then concentrated under reduced pressure. The residue was purified by flash chromatography (6% Methanol in dichloromethane) to afford the title compound as a white solid (35.5 mg, 18%): ¹H NMR (400 MHZ, CDCl₃) δ 0.74–1.69 (6H, m), 2.02–3.63 (4H, m), 5.15–4.72 (4H, m), 6.05–6.79 (4H, 4xs) and 7.11–7.79 (8H, m). ¹⁹F (376 MHz, CDCl₃) δ −225.45, −225.60, −227.42, −228.07, −228.09 and −231.65.

Example 12

[3S/R, (2S)]-5-Fluoro-4-oxo-3-{[1-(phenothiazine-10-carbonyl)piperidine-2-carbonyl]amino}-pentanoic acid ethyl amide

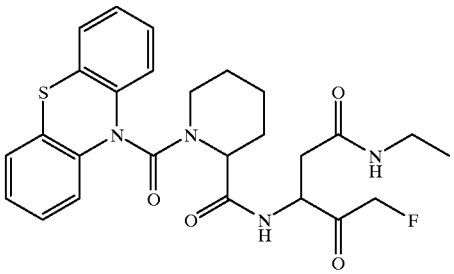

To a stirred mixture of [3S/R, (2S)]-5-fluoro-4-oxo-3-{[1-(phenothiazine-10-carbonyl)piperidine-2-carbonyl]amino}-pentanoic acid (196 mg, 0.4 mmol), prepared as in Example 1, in anhydrous DCM (8 ml), was added Polymer bound EDC (400 mg, 0.8 mmol) and a solution of the ethylamine in THF (0.6 ml of a 2M solution, 12 mmol). The mixture was stirred at room temperature for 16 h then concentrated under reduced pressure. The residue was purified by flash chromatography (2.5% methanol in dichloromethane) to afford the title compound as a white solid (22.7 mg, 11%): $^1$H NMR (400 MHz, CDCl$_3$) δ 1.09–1.39 (3H, m), 1.44–1.66 (6H, m), 2.04–3.66 (7H, m), 4.18–4.76 (6H, m) and 7.10–7.79 (8H, m). $^{19}$F NMR (376 MHz, CDC$_3$) δ −223.32, −223.73, −225.92 and −226.76.

Example 13

[3S/R, (2S)]-5-Fluoro-4-oxo-3-{[1-(phenothiazine-10-carbonyl)piperidine-2-carbonyl]amino}-pentanoic acid diethyl amide

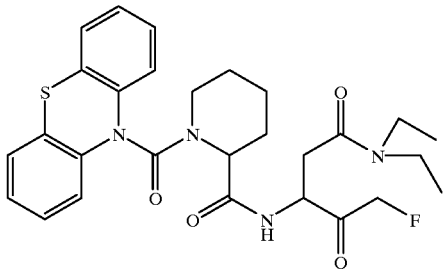

To a stirred mixture of [3S/R, (2S)]-5-fluoro-4-oxo-3-{[1-(phenothiazine-10-carbonyl)piperidine-2-carbonyl]amino}-pentanoic acid (200 mg, 0.4 mmol), prepared as in Example 1, in anhydrous DCM (4 ml), was added carbodiimide (74 mg, 0.44 mmol) and a diethylamine (0.62 ml, 6 mmol). The mixture was stirred at room temperature for 16 h then concentrated under reduced pressure. The residue was purified by flash chromatography (2.5% Methanol in dichloromethane) to afford the title compound as a white solid (25.3 mg, 11%): $^1$H NMR (400 MHz, CDCl$_3$) δ 1.00–1.23 (6H, m), 1.45–1.67 (6H, m), 2.18 (1H, m), 2.74 (1H, m), 2.92 (1H, m), 3.21–3.33 (4H,m), 3.65 (1H, m), 4.68 (1H, m), 4.85 (1H, m), 4.98–5.36 (2H, m) and 7.12–7.95 (8H, m). $^{19}$F NMR (376 MHz, CDCl$_3$) δ −232.37 and −232.72.

Example 14

[3S/R, (2S)]-5-Fluoro-4-oxo-3-{[1-(phenothiazine-10-carbonyl)piperidine-2-carbonyl]amino}-pentanoic acid N,N-dimethyl aminoethylamide

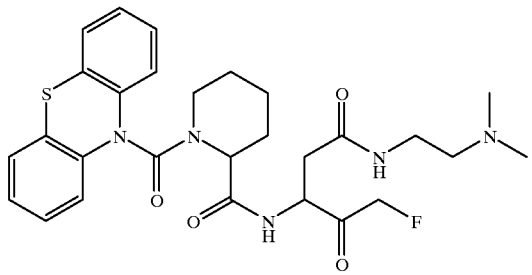

To a stirred mixture of [3S/R, (2S)]-5-fluoro-4-oxo-3-{[1-(phenothiazine-10-carbonyl)piperidine-2-carbonyl]amino}-pentanoic acid (100 mg, 0.2 mmol), prepared as in Example 1, in anhydrous DCM (5 ml), was added Polymer bound EDC (300 mg, 0.6 mmol) and N,N-dimethyl propylamide (0.88 ml, 6 mmol). The mixture was stirred at room temperature for 16 h then concentrated under reduced pressure. The residue was purified by flash chromatography (2% Methanol in dichloromethane) to afford the title compound as a white solid (16.5 mg, 14%): $^1$H NMR (400 MHz, CDCl$_3$) δ 1.48–1.68 (6H, m), 2.20–2.40 (8H, m), 2.60 (1H, m), 2.71–3.06 (3H, m); 3.73 (1H, m), 4.01 (1H, m), 4.16–4.38 (2H, m), 4.62 (1H, m), 4.75 (1H, m), 6,96 (1H, m) and 7.11–7.77 (8H, m). $^{19}$F NMR (376 MHz, CDCl$_3$) δ−222.48 and −222.63.

Example 15

[3S/R, (2S)]-5-Fluoro-4-oxo-3-{[1-(phenothiazine-10-carbonyl)piperidine-2-carbonyl]amino}-pentanoic acid N methyl piperazine amide

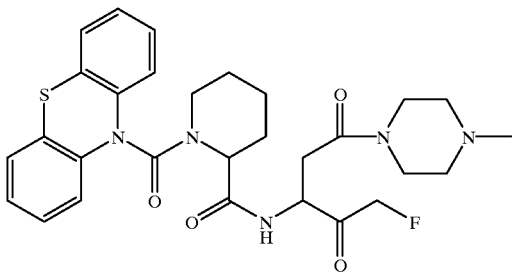

To a stirred mixture of [3S/R, (2S)]-5-fluoro-4-oxo-3-{[1-(phenothiazine-10-carbonyl)piperidine-2-carbonyl]amino}-pentanoic acid (200 mg, 0.4 mmol), prepared as in Example 1, in anhydrous THF (4 ml), was added EDC (84 mg, 0.44 mmol) and N methyl piperazine (0.88 ml, 8 mmol). The mixture was stirred at room temperature for 16 h then concentrated under reduced pressure. The residue was purified by flash chromatography (2% Methanol in dichloromethane) to afford the title compound as a white solid (33 mg, 14%): $^1$H NMR (400 MHz, CDCl$_3$) δ 1.47–1.70 (6H, m), 2.13–2.50 (7H, m), 2.75 (1H, m), 2.90 (1H, m), 3.19 (1H, m), 3,41–3.65 (5H, m), 4.66 (1H, m), 4.86 (1H, m), 4.97–5.34 (2H, m), 7.12–7.18 (2H, m), 7.27–7.37 (3H, m), 7.23–7.54 (1H, m) and 7.74–7.78 (2H, m). $^{19}$F NMR (376 MHz, CDCl$_3$) δ −232.24 and −232.52.

The compounds of this invention are designed to inhibit caspases. Therefore, the compounds of this invention may be assayed for their ability to inhibit apoptosis, the release of IL-β or caspase activity directly. Assays for each of the activities are known in the art and are described below in detail in the Testing section.

According to another embodiment, the invention provides a composition comprising a compound of this invention or a pharmaceutically acceptable salt thereof, as described above, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intraarticular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The above-described compositions are particularly useful in therapeutic applications relating to an IL-1 mediated disease, an apoptosis mediated disease, an inflammatory disease, an autoimmune disease, a destructive bone disorder, a proliferative disorder, an infectious disease, a degenerative disease, a disease associated with cell death, an excess dietary alcohol intake disease, a viral mediated disease, uveitis, inflammatory peritonitis, osteoarthritis, pancreatitis, asthma, adult respiratory distress syndrome, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, chronic active hepatitis, myasthenia gravis, inflammatory bowel disease, Crohn's disease, psoriasis, atopic dermatitis, scarring, graft vs host disease, organ transplant rejection, osteoporosis, leukemias and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, septic shock, burns, Shigellosis, Alzheimer's disease, Parkinson's disease, Huntington's disease, Kennedy's disease, prion disease, cerebral ischemia, epilepsy, myocardial ischemia, acute and chronic heart disease, myocardial infarction, congestive heart failure, atherosclerosis, coronary artery bypass graft, spinal muscular atrophy, amyotrophic lateral sclerosis, multiple sclerosis, HIV-related encephalitis, aging, alopecia, neurological damage due to stroke, ulcerative colitis, traumatic brain injury, spinal cord injury, hepatitis-B, hepatitis-C, hepatitis-G, yellow fever, dengue fever, or Japanese encephalitis, various forms of liver disease, renal disease, polyaptic kidney disease, H. pylori-associated gastric and duodenal ulcer disease, HIV infection, tuberculosis, and meningitis. The compounds and compositions are also useful in treating complications associated with coronary artery bypass grafts and as a component of immunotherapy for the treatment of various forms of cancer.

The amount of compound present in the above-described compositions should be sufficient to cause a detectable decrease in the severity of the disease or in caspase activity and/or cell apoptosis, as measured by any of the assays described in the examples.

The compounds of this invention are also useful in methods for preserving cells, such as may be needed for an organ transplant or for preserving blood products. Similar uses for caspase inhibitors have been reported (Schierle et al., *Nature Medicine*, 1999, 5, 97). The method involves treating the cells or tissue to be preserved with a solution comprising the caspase inhibitor. The amount of caspase inhibitor needed will depend on the effectiveness of the inhibitor for the given cell type and the length of time required to preserve the cells from apoptotic cell death.

According to another embodiment, the compositions of this invention may further comprise another therapeutic agent. Such agents include, but are not limited to, thrombolytic agents such as tissue plasminogen activator and streptokinase. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition. As used herein, the term "patient" refers to a warm-blooded animal, such as for example, rats, mice, dogs, cats, guinea pigs, and primates such as humans.

In a preferred embodiment, the invention provides a method of treating a mammal, having one of the aforementioned diseases, comprising the step of administering to said mammal a pharmaceutically acceptable composition described above. In this embodiment, if the patient is also administered another therapeutic agent or caspase inhibitor, it may be delivered together with the compound of this invention in a single dosage form, or, as a separate dosage form. When administered as a separate dosage form, the other caspase inhibitor or agent may be administered prior to, at the same time as, or following administration of a pharmaceutically acceptable composition comprising a compound of this invention.

In order that this invention be more fully understood, the following biological testing examples are set forth. These examples are for the purpose of illustration only and are not to be construed as limiting the scope of the invention in any way.

Biolgical Testing Examples

Example 16

Enzyme Assays

The assays for caspase inhibition are based on the cleavage of a fluorogenic substrate by recombinant, purified human Caspases -1,-3, or -8. The assays are run in essentially the same way as those reported by Garcia-Calvo et al. (*J. Biol. Chem.* 273 (1998), 32608–32613), using a substrate specific for each enzyme. The substrate for Caspase-1 is Acetyl-Tyr-Val-Ala-Asp-amino-4-methylcoumarin. The substrate for Caspases -3, and -8 is Acetyl-Asp-Glu-Val-Asp-amino-4-methylcoumarin.

The observed rate of enzyme inactivation at a particular inhibitor concentration, $k_{obs}$, is computed by direct fits of the data to the equation derived by Thornberry et al. (*Biochemistry* 33 (1994), 3943–3939) using a nonlinear least-squares analysis computer program (PRISM 2.0; GraphPad software). To obtain the second order rate constant, kinact, kobs values are plotted against their respective inhibitor concentrations and $k_{inact}$ values are subsequently calculated by computerized linear regression.

The compounds tested under Example 16 possess $k_{inact}>50000$ $M^{-1}s^{-1}$ against caspase-1, caspase-3 and caspase-8.

Example 17

Inhibition of IL-1β secretion from Mixed Population of Peripheral Blood Mononuclear Cells (PBMC)

Processing of pre-IL-1β by caspase-1 may be measured in cell culture using a variety of cell sources. Human PBMC obtained from healthy donors provides a mixed population of lymphocyte and mononuclear cells that produce a spectrum of interleukins and cytokines in response to many classes of physiological stimulators.

Experimental Procedure

The test compound is dissolved in Dimethyl Sulphoxide (DMSO,Sigma #D-2650) to give a 100 mM stock solution. This is diluted in complete medium consisting of RPMI containing 10% heat inactivated FCS (Gibco BRL #10099–141), 2 mM L-Glutamine (Sigma, #G-7513), 100 U penicillin and 100 μg/ml streptomycin (Sigma #P-7539). The final concentration range of test compound is from 100 μM down to 6 nM over eight dilution steps. The highest concentration of test compound is equivalent to 0.1% DMSO in the assay.

Human PBMC are isolated from Buffy Coats obtained from the blood bank using centrifugation on Ficoll-Paque leukocyte separation medium (Amersham, #17–1440–02) and the cellular assay is performed in a sterile 96 well flat-bottomed plate (Nunc). Each well contains 100 μl of the cell suspension, 1×10$^5$ cells, 50 μl of compound dilutions and 50 μl of LPS (Sigma #L-3012) at 50 ng/ml final concentration. Controls consist of cells +/−LPS stimulation and a serial dilution of DMSO diluted in the same way as compound. The plates are incubated for 16–18 h at 37° C. in 5% $CO_2$ & 95% humidity atmosphere.

After 16–18 h the supernatants are harvested after centrifuging the plates at 100×g at 18° C. for 15 min and assayed for their IL-1μ content. Measurement of mature IL-1μ in the supernatant is performed using the Quantikine kits (R&D Systems) according to manufacturer's instructions. Mature IL-1β levels of about 600–1500 pg/ml are observed for PBMCs in positive control wells.

The inhibitory potency of the compounds may be represented by an $IC_{50}$ value, which is the concentration of inhibitor at which 50% of the mature IL-1β is detected in the supernatant as compared to the positive controls.

Selected compounds from Table 1 were tested according to Example 17 and found to provide an $IC_{50}$ value less than 2 μM for inhibition of IL-1β secretion from PBMC.

Example 18

Anti-Fas Induced Apoptosis Assay

Cellular apoptosis may be induced by the binding of Fas ligand (FasL) to its receptor, CD95 (Fas). CD95 is one of a family of related receptors, known as death receptors, which can trigger apoptosis in cells via activation of the caspase enzyme cascade. The process is initiated by the binding of the adapter molecule FADD/MORT-1 to the cytoplasmic domain of the CD-95 receptor-ligand complex. Caspase-8 then binds FADD and becomes activated, initiating a cascade of events that involve the activation of downstream caspases and subsequent cellular apoptosis. Apoptosis can also be induced in cells expressing CD95 eg the Jurkat E6.1 T cell lymphoma cell line, using an antibody, rather than FasL, to crosslink the cell surface CD95. Anti-Fas-induced apoptosis is also triggered via the activation of caspase-8. This provides the basis of a cell-based assay to screen compounds for inhibition of the caspase-8-mediated apoptotic pathway.

Experimental Procedure

Jurkat E6.1 cells are cultured in complete medium consisting of RPMI-1640 (Sigma No) +10% foetal calf serum (Gibco BRL No.10099–141) +2mM L-glutamine (Sigma No. G-7513). The cells are harvested in log phase of growth. 100 ml Cells at 5–8×10$^5$ cells/ml are transferred to sterile 50 ml Falcon centrifuge tubes and centrifuged for 5 minutes at 100 xg at room temperature. The supernatant is removed and the combined cell pellets resuspended in 25 ml of complete medium. The cells are counted and the density adjusted to 2×10$^6$cells/ml with complete medium.

The test compound is dissolved in dimethyl sulphoxide (DMSO)(Sigma No. D-2650) to give a 100 mM stock solution. This is diluted to 400 μM in complete medium, then serially diluted in a 96-well plate prior to addition to the cell assay plate.

100 μl of the cell suspension (2×10$^6$ cells) is added to each well of a sterile 96-well round-bottomed cluster plate (Costar No. 3790). 50 μl of compound solution at the appropriate dilution and 50 μl of anti-Fas antibody, clone CH-11 (Kamiya No.MC-060) at a final concentration of 10 ng/ml, are added to the wells. Control wells are set up minus antibody and minus compound but with a serial dilution of DMSO as vehicle control. The plates are incubated for 16–18 hrs at 37° C. in 5% $CO_2$ and 95% humidity.

Apoptosis of the cells is measured by the quantitation of DNA fragmentation using a 'Cell Death Detection Assay' from Boehringer-Mannheim, No. 1544 675. After incubation for 16–18 hrs the assay plates are centrifuged at 100×g at room temperature for 5 minutes. 150 μl of the supernatant are removed and replaced by 150 μl of fresh complete medium. The cells are then harvested and 200 μl of the lysis buffer supplied in the assay kit are added to each well. The cells are triturated to ensure complete lysis and incubated for 30 minutes at 4° C. The plates are then centrifuged at 1900×g for 10 minutes and the supernatants diluted 1:20 in the incubation buffer provided. 100 μl of this solution is then assayed exactly according to the manufacturer's instructions supplied with the kit. $OD_{405}$ nm is measured 20 minutes after addition of the final substrate in a SPECTRAmax Plus plate reader (Molecular Devices). $OD_{405}$ nm is plotted versus compound concentration and the $IC_{50}$ values for the compounds are calculated using the curve-fitting program SOFTmax Pro (Molecular Devices) using the four parameter fit option. Selected compounds from Table 1 were tested according to Example 18 and found to provide an $IC_{50}$ value less than 100 nM for the activity in the FAS induced apoptosis assay.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A compound of formula I:

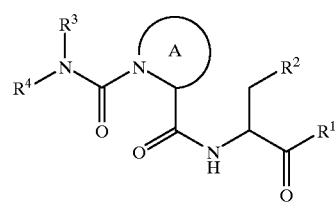

I wherein:

Ring A is an optionally substituted piperidine ring;

$R^1$ is hydrogen, CN, $CHN_2$, R, or $CH_2Y$;

R is an optionally substituted group selected from an aliphatic group, an aryl group, or an aralkyl group;

Y is an electronegative leaving group;

$R^2$ is
  i) $CO_2H$, or an ester or an amide thereof; or $R^2$ is an isostere of said $CO_2H$; or
  ii) $CH_2CO_2H$, or an ester or an amide thereof; or $R^2$ is an isostere of said $CH_2CO_2H$;
$R^3$ is hydrogen, an optionally substituted aryl group, an optionally substituted aralkyl group or an optionally substituted $C_{1-6}$ aliphatic group; and
$R^4$ is an optionally substituted group selected from an aryl group or a heterocyclyl group, or $R^3$ and $R^4$ taken together with the nitrogen to which they are attached optionally form a substituted or unsubstituted monocyclic, bicyclic or tricyclic ring.

2. The compound according to claim 1 wherein:
$R^1$ is $CH_2Y$ where Y is an electronegative leaving group; and
$R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

3. The compound of claim 1, wherein:
$R^1$ is $CH_2Y$ where Y is an electronegative leaving group.

4. The compound according to claim 1 wherein the compound is selected from compound listed in Table 1 below:

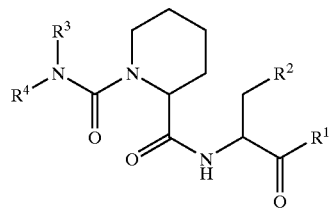

Ia

| No. | $R^1$ | $R^2$ | Ring A Type | $R^3R^4N—$ |
|---|---|---|---|---|
| I-1 | $CH_2F$ | $CO_2H$ | Ia | phenothiazin-10-yl |
| I-2 | $CH_2F$ | $CO_2H$ | Ia | 2-chlorophenothiazin-10-yl |
| I-3 | $CH_2F$ | $CO_2H$ | Ia | 3-chlorophenothiazin-10-yl |
| I-4 | $CH_2F$ | $CO_2H$ | Ia | 3,4-dichlorophenothiazin-10-yl |
| I-5 | $CH_2F$ | $CO_2H$ | Ia | 2,7-dichlorophenothiazin-10-yl |

-continued
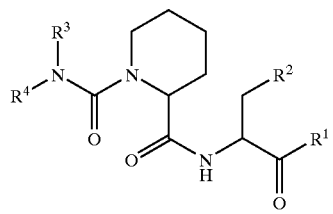
Ia
| No. | R¹ | R² | Ring A Type | R³R⁴N— |
|---|---|---|---|---|
| I-6 | CH₂F | CO₂H | Ia | 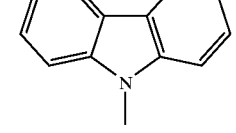 |
| I-7 | CH₂F | CO₂H | Ia | 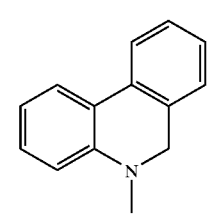 |
| I-8 | CH₂F | CO₂H | Ia | 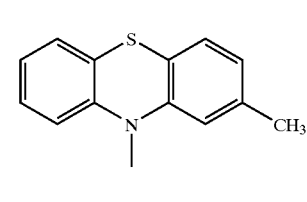 |
| I-9 | CH₂F | CO₂H | Ia | 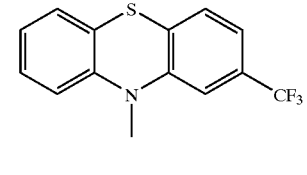 |
| I-10 | CH₂F | CO₂H | Ia | 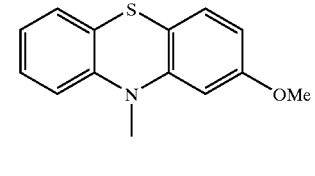 |
| I-11 | CH₂F | CO₂NH₂ | Ia | 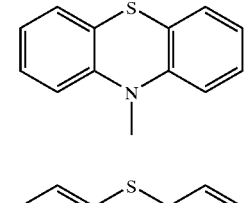 |
| I-12 | CH₂F | CO₂NHEt | Ia | 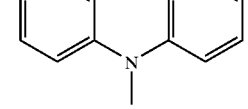 |

-continued

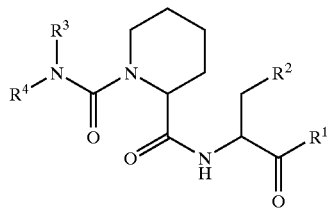

Ia

| No. | R¹ | R² | Ring A Type | R³R⁴N— |
|---|---|---|---|---|
| I-13 | $CH_2F$ | $CO_2NEt_2$ | Ia | 10-methylphenothiazin-10-yl |
| I-14 | $CH_2F$ | $CONHCH_2CH_2N(CH_3)_2$ | Ia | 10-methylphenothiazin-10-yl |
| I-15 | $CH_2F$ | $CO_2H$ | Ib | 10-methylphenothiazin-10-yl |
| I-16 | $CH_2F$ | $CO_2H$ | Ic | 10-methylphenothiazin-10-yl |
| I-17 | $CH_2F$ | $CO_2H$ | Ib | 2-chloro-10-methylphenothiazin-10-yl |
| I-18 | $CH_2F$ | $CO_2H$ | Ic | 2-chloro-10-methylphenothiazin-10-yl |
| I-19 | $CH_2F$ | $CO_2H$ | Ia | 10-methylacridin-10-yl |
| I-20 | $CH_2F$ | $CO_2H$ | Ia | 9-hydroxy-10-methylacridin-10-yl |

-continued
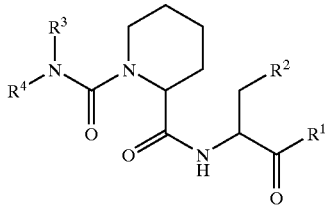
Ia
| No. | R¹ | R² | Ring A Type | R³R⁴N— |
|---|---|---|---|---|
| I-21 | CH₂F | CO₂H | Ia | 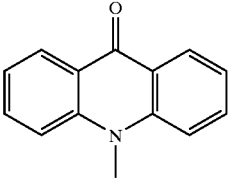 |
| I-22 | CH₂F | CO₂H | Ia | 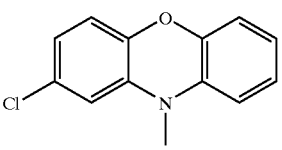 |
| I-23 | CH₂F | CO₂H | Ia | 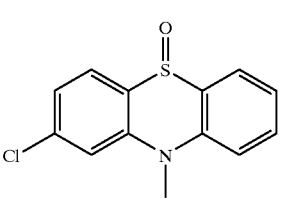 |
| I-24 | CH₂F | CO₂H | Ia | 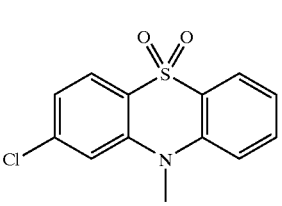 |
| I-25 | CH₂F | CO₂H | Ia | 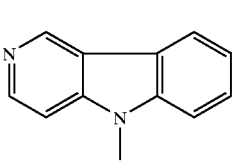 |
| I-26 | CH₂F | CO₂H | Ia | 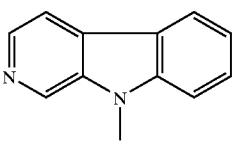 |
| I-27 | CH₂F | CO₂H | Ia | 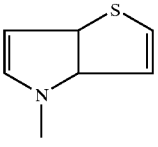 |

-continued

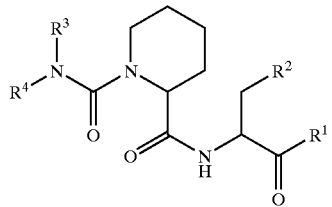

Ia

| No. | R¹ | R² | Ring A Type | R³R⁴N— |
|---|---|---|---|---|
| I-28 | CH₂F | CO₂H | Ia | (1-methylindol-3-yl) |
| I-29 | CH₂F | CO₂H | Ia | (6-chloro-1-methylindol-3-yl) |
| I-30 | CH₂F | CO₂H | Ia | (10-methyl-pyrido-phenothiazinyl) |

5. The compound according to claim 1, wherein
   $R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

6. The compound according to claim 5, wherein $R^3$ and $R^4$, taken together with the nitrogen to which they are attached, form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

7. A compound of formula I:

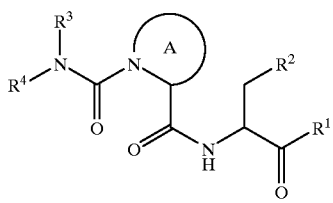

I wherein:
Ring A is an optionally substituted piperidine ring;
$R^1$ is hydrogen. CN, CHN₂, R, or CH₂Y;
R is an optionally substituted group selected from an aliphatic group, an aryl group, or an aralkyl group;
Y is an electronegative leaving group;
$R^2$ is:
   i) CO₂H, or an ester or an amide thereof; or
   ii) CH₂CO₂H, or an ester or an amide thereof;
$R^3$ is hydrogen, an optionally substituted aryl group, an optionally substituted aralkyl group or an optionally substituted $C_{1-6}$ aliphatic group; and
$R^4$ is an optionally substituted group selected from an aryl group or a heterocyclyl group, or $R^3$ and $R^4$ taken together with the nitrogen to which they are attached optionally form a substituted or unsubstituted monocyclic, bicyclic or tricyclic ring.

8. The compound according to claim 7, wherein
$R^1$ is $CH_2Y$ where Y is an electronegative leaving group; and
$R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline. isoquinoline, cinnoline, phthalazine, quinazoline, quinoxaline, 1,8-naphthyridine, pteridine, quinuclidine, and phenazine.

9. The compound according to claim 7, wherein
$R^1$ is $CH_2Y$ where Y is an electronegative leaving group.

10. The compound according to claim 7, wherein
$R^4$ is an optionally substituted group selected from an aryl group or a heterocyclyl group, or $R^3$ and $R^4$, taken together with the nitrogen to which they are attached, optionally form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

11. The compound according to claim 10, wherein
$R^3$ and $R^4$, taken together with the nitrogen to which they are attached, form a ring selected from the group consisting of indole, isoindole, indoline, indazole, purine, benzimidazole, benzthiazole, imidazole, imidazoline, thiazole, pyrrole, pyrrolidine, pyrroline, pyrazole, pyrazoline, pyrazolidine, triazole, piperidine, morpholine, thiomorpholine, piperazine, carbazole, phenothiazine, phenoxazine, phenanthridine, acridine, purine, quinolizine, quinoline, isoquinoline, cinnoline, phthalazine, quinazoline, quinoxaline, 1,8-naphthyridine, pteridine, quinuclidine, and phenazine.

12. The compound according to claim 1, wherein —$CH_2Y$ is —$CH_2F$.

13. The compound according to claim 2, wherein —$CH_2Y$ is —$CH_2F$.

14. The compound according to claim 7, wherein —$CH_2Y$ is —$CH_2F$.

15. The compound according to claim 8, wherein —$CH_2Y$ is —$CH_2F$.

16. The compound according to claim 1, wherein $R^2$ is $CO_2H$, or an ester or an amide thereof; or $R^2$ is an isostere of said $CO_2H$.

17. A pharmaceutical composition comprising a compound according to any one of claims 1–3, 4–15 or 16 and a pharmaceutically acceptable carrier.

18. A method for treating a disease in a patient that is alleviated by treatment with a caspase inhibitor, which method comprises administering to a patient in need of such a treatment a therapeutically effective amount of a compound according to claim 1.

19. A method of treating an inflammatory disease, an autoimmune disease, a destructive bone disorder, acute and chronic heart disease, uveitis, inflammatory peritonitis, systemic lupus erythematosus, diabetes, Crohn's disease, ulcerative colitis, atopic dermatitis, organ transplant rejection, hemorrhagic shock, congestive heart failure, osteoarthritis, rheumatoid arthritis, psoriasis, glomerulonephritis, graft vs host disease, inflammatory bowel disease, sepsis, septic shock, burns, organ apoptosis after burn injury, stroke, cerebral ischemia, traumatic brain injury, neurological damage due to stroke, spinal cord injury, amyotrophic lateral sclerosis, multiple sclerosis, myocardial infarct, myocardial ischemia, atherosclerosis, acute respiratory failure, adult respiratory distress syndrome, pancreatitis, various forms of liver and renal disease, an excess dietary alcohol intake disease, chronic active hepatitis, hepatitis-B, hepatitis-C, coronary artery bypass graft or a treatment for complications associated with coronary bypass grafts, or an immunotherapy for the treatment of various forms of cancer, in a patient that is alleviated by treatment with a caspase inhibitor, comprising administering to a patient in need of such a treatment a therapeutically effective amount of a compound or formula I:

20. The method according to claim 19 wherein said method comprises administering to a patient in need of such a treatment a therapeutically effective amount of a compound according to any one of claims 1–3, 15–26, or 31.

21. The method according to claim 19 wherein the compound is used to treat complications associated with coronary artery bypass grafts.

22. The method according to any one of claims 1–3, 4–15, or 16 wherein the compound is used for the preservation of cells, said method comprising the step of bathing the cells in a solution of the compound or a pharmaceutically acceptable derivative thereof.

23. The method according to any one of claims 1–3, 4–15, or 16 wherein the compound is used for an organ transplant or for preserving blood products.

24. The method according to claim 19 wherein the compound is used as a component of immunotherapy for the treatment of cancer.

* * * * *